United States Patent
Matsumoto

(10) Patent No.: US 7,420,575 B2
(45) Date of Patent: Sep. 2, 2008

(54) IMAGE PROCESSING APPARATUS, IMAGE PROCESSING METHOD AND IMAGE PROCESSING PROGRAM

(75) Inventor: Kazuhiko Matsumoto, Tokyo (JP)

(73) Assignee: Ziosoft, Inc., Tokyo (JP)

( * ) Notice: Subject to any disclaimer, the term of this patent is extended or adjusted under 35 U.S.C. 154(b) by 424 days.

(21) Appl. No.: 11/000,464

(22) Filed: Nov. 29, 2004

(65) Prior Publication Data
US 2006/0007244 A1    Jan. 12, 2006

(30) Foreign Application Priority Data
Jun. 3, 2004    (JP)    ............... 2004-165722

(51) Int. Cl.
G09G 5/00    (2006.01)
(52) U.S. Cl. .................. 345/646; 345/619; 345/660; 345/672; 345/687
(58) Field of Classification Search .......... 345/664, 345/665, 672, 676, 684, 687, 688, 646; 715/784–787, 715/799–800, 864, 866; 382/128
See application file for complete search history.

(56) References Cited

U.S. PATENT DOCUMENTS 6,182,133 B1    1/2001    Horvitz

2005/0104904 A1 *  5/2005  Numata et al. ............. 345/660
2006/0187241 A1 *  8/2006  Boler et al. ................. 345/660
2006/0192780 A1 *  8/2006  Lantin ....................... 345/427

FOREIGN PATENT DOCUMENTS

| JP | 6-65944 | 9/1994 |
| JP | 9-62861 | 3/1997 |
| JP | 11-258977 | 9/1999 |
| JP | 2001034775 | * 2/2001 |
| JP | 2003-208633 | 7/2003 |
| JP | 2003-233600 | 8/2003 |

* cited by examiner

Primary Examiner—Chante Harrison
(74) Attorney, Agent, or Firm—Pearne & Gordon LLP

(57) ABSTRACT

An image processing apparatus comprises: a predicted information storage section which stores predicted information that indicates an operation content predicted for an image of a target operation; a predicted image generating portion which generates a predicted image which corresponds to the image of the target operation based on a predicted information; a control section which detects whether input operation content matches the operation contents in the predicted information; and a display control section which displays a predicted image generated by the predicted image generating portion when the control section detects the matching of the operation contents.

13 Claims, 9 Drawing Sheets

US 7,420,575 B2

IMAGE PROCESSING APPARATUS, IMAGE PROCESSING METHOD AND IMAGE PROCESSING PROGRAM

This application claims foreign priority based on Japanese Patent application No. 2004-165722, filed Jun. 3, 2004, the contents of which is incorporated herein by reference in its entirety.

BACKGROUND OF THE INVENTION

1. Field of the Invention

The present invention relates to an image processing apparatus, an image processing method and an image processing program.

2. Description of the Related Art

Conventionally, image diagnosis, whereby the internal structure of a human body can be directly observed, is performed by employing two dimensional images obtained by a CT (Computed Tomography) apparatus or an MRI (Magnetic Resonance Imaging) apparatus. Furthermore, volume rendering has recently begun to be employed, where three dimensional space is represented by voxels, the volume elements, which cuts the three dimensional space into small grids, based on a digital data which is generated by a collection of two dimensional images obtained by a CT apparatus or an MRI apparatus and any other medical imaging device. With this technique, internal human body structure can be visualized that is hardly understood only by studying each two dimensional image.

Ray casting is known as one volume rendering technique, where virtual ray is emitted to an object from a virtual starting point, and an image is formed on a virtual projection plane by the virtual ray reflected from the inside of the object, and whereby the three dimensional internal structure of the object is seen through. When having a diagnosis based on an image generated by ray casting, since the internal structure of a human body is extremely complicated, precision of the shape of the internal structure must be raised by reducing the sizes of voxels. However, as the precision is increased, the amount of data increases enormously, and an extended period of time is required to perform the calculation process for generating image data.

For an actual image diagnosis, a sequence of operation is repeated, where a target portion is displayed on a monitor screen, an affected part is observed in detail by repeating the operation such as gradually changing a display angle or gradually moving the display position, and finally the diagnostic information is reviewed in a report such as a diagnosis result.

In an image processing apparatus that performs this sequence of operation, a heavy load is imposed during the image data generating process, and a long time elapses before display data is obtained. However, once the data is displayed on a screen, no other processing is required but the apparatus simply waits to perform the next operation. As a consequence, an apparatus has been developed that effectively utilizes a period of time during which the imposed load is small, and that thereby reduces the time required for the acquisition of the next data to be displayed, as described in U.S. Pat. No. 6,182,133.

According to the display apparatus disclosed in U.S. Pat. No. 6,182,133, during a nonoperational period, the browser of a client computer obtains and stores a Web page, or its component in a local cache memory in advance, and the display apparatus is constructed as to visually notify a user by a visual sign via a graphical user interface that the new Web page has been extracted. During a period of time wherein the network load is low, an unused computer resource can be effectively utilized and a new Web page can be displayed quickly.

According to the display apparatus disclosed in U.S. Pat. No. 6,182,133, however, the browser of the client computer merely obtains and stores a Web page provided by a server computer in advance. A new image is neither created nor displayed.

Further, in image diagnosis, since a targeted human body differs in every diagnosis and an image is not provided in advance, and an image data for volume rendering image has to be generated after an instruction of the operator is input by calculation in accordance with the instruction. For example, when panning the display position, as shown in FIGS. 9A and 9B, after an instruction of the operator is input, a new image data is reconstructed by performing a complicated calculation using an enormous amount of data. Therefore, an extended period of time is required to display an image, and as is shown in FIG. 9B, a part of the image is darkened.

As a result, the conventional image processing apparatus not only contributes stress to the operator, but also degrades efficiency of diagnosis because an operation is halted until an image is displayed on a screen.

SUMMARY OF THE INVENTION

Considering the conventional invention, an object of the present invention is to provide an image processing apparatus, an image processing method and an image processing program, whereby an image which corresponds to a content of an operation is promptly displayed.

According to the invention, an image processing apparatus comprises a predicted information storage section for storing a predicted information indicating operation contents which are predicted for an image of a target operation, a predicted image generating section for generating a predicted image based on the predicted information so as to be corresponding to the image of the target operation, and an image display control section for displaying an image based on said generated predicted image when operation contents of an input operation match those of said predicted information.

With this configuration, since a predicted image generating section is provided that generates a predicted image which corresponds to an image in a target of operation based on a predicted information, an image generated in advance can be displayed without the generating of an image being required for each operation. Therefore, an image which corresponds to the content of the operation can be promptly displayed.

The image processing apparatus of the invention further comprises a history information storage section for storing a history information which indicates the operation contents performed in the past, wherein the predicted information is generated based on the history information. With this configuration, when the content of the operation is input as same as that in the history information, an image which corresponds to the content of the operation can be promptly displayed.

Further, in the image processing apparatus of the invention, the predicted information is generated based on a current operating state. With this configuration, since an image generated in advance based on the current operating state is displayed, an image which corresponds to the content of the operation can be promptly displayed.

For the image processing apparatus of the invention, the predicted information is a preceding operation content, and the predicted image generating section generates one or more predicted image based on the preceding operation content. With this configuration, the probability can be increased that displays an image which reflects the intent of the operator.

For the image processing apparatus of the invention, the predicted information is an operation information obtained by changing a selected one-dimensional parameter, and further the predicted image generating section generates the predicted image based on the operation information obtained by changing the selected one-dimensional parameter. With this configuration, the dimension of the next operation that is predicted to be beyond numbers and represented multi-dimensionally is reduced to a single dimension. Therefore, the number of calculations required for the generating of a predicted image can be considerably reduced to a realistic and available number, and an appropriate predicted image can be generated within a realistic period of time so that an image which corresponds to the content of the operation can be promptly displayed.

For the image processing apparatus of the invention, the predicted information is an operation information obtained by changing a selected two-dimensional parameter, and the predicted image generating section generates the predicted image based on the operation information obtained by changing the selected two-dimensional parameter. With this configuration, the dimension of the next operation that is predicted to be beyond numbers and represented multi-dimensionally is reduced to two dimensions. Therefore, the number of calculations required for the generating of a predicted image can be considerably reduced to a realistic and available number, and an appropriate predicted image can be generated within a realistic period of time so that an image which corresponds to the content of the operation can be promptly displayed.

For the image processing apparatus of the invention, when a type of the image of the target operation is a multi planar reconstruction image, the one-dimensional parameter of the operation information which is obtained by changing the selected one-dimensional parameter is a parameter for a cut position of a displayed slice of a multi planar reconstruction image. With this configuration, a specific portion can be observed in detail while changing the cutting position of the displayed slice of the MPR image.

For the image processing apparatus of the invention, when a type of the image of the target position is a moving picture, the one-dimensional parameter of the operation information which is obtained by changing the selected one-dimensional parameter is used for determining a display frame for the moving picture. With this configuration, the moving image can be smoothly moved.

For the image processing apparatus of the invention the one-dimensional parameter of the operation information which is obtained by changing the one-dimensional parameter is used for determining a rotational angle. Further, for the image processing apparatus of the invention, the one-dimensional parameter for the operation information which is obtained by changing the one-dimensional parameter is used for determining a scale factor. Furthermore, for the image processing apparatus of the invention, the one-dimensional parameter of the operation information which is obtained by changing the one-dimensional parameter is one of the parameters for defining a color look-up transformation function. In addition, for the image processing apparatus of the invention, the one-dimensional parameter of the operation information which is obtained by changing the one-dimensional parameter is one of the parameters for defining an opacity function. Moreover, for the image processing apparatus of the invention, the two-dimensional parameter of the operation information which is obtained by changing the two-dimensional parameter is used for determining a vertical or horizontal relative position of a pan operation.

For the image processing apparatus of the invention, the predicted image generating section generates the volume rendering image that is obtained by the pan operation which is determined by changing the two-dimensional parameter, when the preceding operation content is a pan operation such that a volume rendering image of the target operation is moved two-dimensionally parallel to a projection plane without changing the projection angle of the volume rendering image. With this configuration, when an image is displayed by the pan operation just by extracting only a portion that fits in a screen, generating an image of the remaining outer portion of the image as a predicted image in advance enables the pan operation to be smoothly coped with.

For the image processing apparatus of the invention, the history information storage section is used to store operating history information for each operator. With this configuration, since the history information storage section stores the operating history information for every operator, the image processing apparatus can cope with multiple users.

For the image processing apparatus of the invention, for the generating of a predicted image, the predicted image generating section generates the predicted image by distributing a calculation load, requiring for generating the predicted image, to a plurality of image processing apparatuses connected via a network. With this configuration, since the calculation resources of the other image processing apparatuses are employed, the image generating load imposed on the image processing apparatus can be reduced.

The image processing apparatus of the invention performs a volume rendering process based on a voxel data.

A method of image processing comprising generating a predicted image which corresponds to an image of a target operation based on a predicted information indicating operation contents which are predicted for the image of the target operation, displaying an image based on said generated predicted image when operation contents of an input operation match those of said predicted information.

Further, a computer product for enabling a computer to perform image processing of the present invention, comprising a computer program operative to perform the following steps of storing a predicted information indicating operation contents which are predicted for an image of a target operation, generating a predicted image based on the predicted information so as to be corresponding to the image of the target operation, and displaying an image based on said generated predicted image when operation contents of an input operation match those of said predicted information.

DESCRIPTION OF THE PRFERED EMBODIMENTS

An image processing apparatus will now be described according to the preferred embodiment of the present invention. It should be noted that the image processing apparatus in this invention handles a medical image drawn mainly on the basis of voxel data, and the image processing is performed by a computer program.

Figure 1:
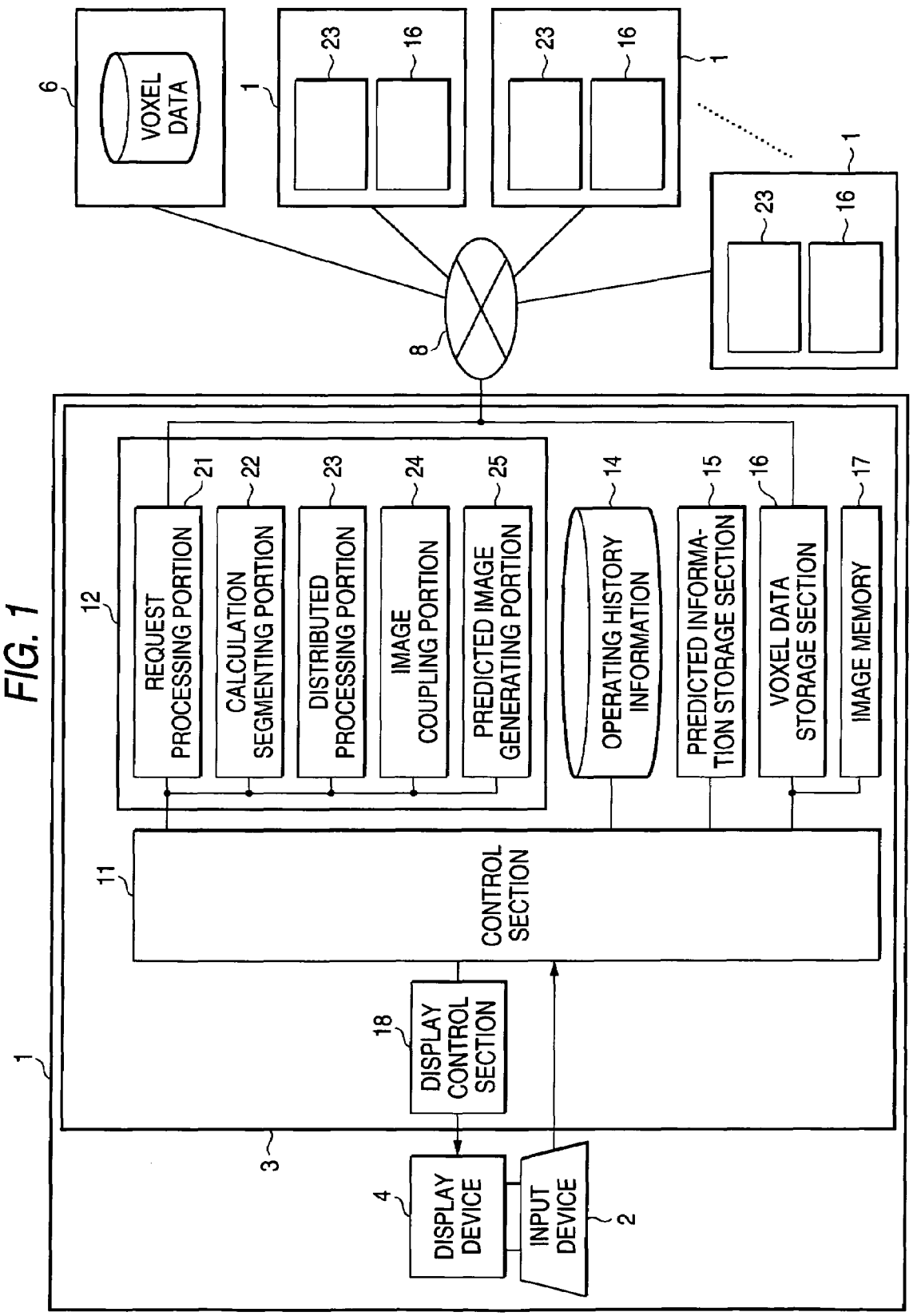
FIG. 1 is a functional block diagram showing an image processing apparatus according to one embodiment of the present invention.

FIG. 1 is a functional block diagram showing the image processing apparatus according to the embodiment of the present invention. In FIG. 1, an image processing system 1 comprises: an input device 2, for the input of an operation by an operator, such as a doctor; an image processing apparatus 3, for generating an image in accordance with the operation input from the input device 2; and a display device 4, for displaying a medical image generated by the image processing apparatus 3. The image processing system 1 is connected, via a communication line 8, to a storage server 6, which stores a medical image that is obtained by medial image diagnosing equipment, such as a CT apparatus and an MRI apparatus, as a voxel data, and also connected to a plurality of other image processing systems. The image processing system 1 can utilize the calculation resources of the other image processing systems via an in-hospital network, a LAN, constituted by the communication line 8.

The image processing apparatus 3 comprises a control section 11 which is connected to: an image generating section 12, which generates an image data for an image to be displayed in accordance with an operation input from the input device 2; an operating history information storage section 14, which stores the contents of operations performed in the past for every operator; a predicted information storage section 15, which stores an operation predicted as the next following operation carried out by operators; a voxel data storage section 16, which stores a data list that is transferred from the storage server 6 for a distributed volume rendering process; an image memory 17, which loads the image data for distributed volume rendering process transferred from the image generating section 12 and each image processing system; and a display control section 18, which displays an image on the display device 4 based on the image data loaded in the image memory 17.

The image generating section 12 includes a predicted image generating portion 25, which generates a predicted image which corresponds to an image of a target operation based on a predicted information. The control section 11 detects whether the contents of the input operation match the contents of an operation of the operating history information. When the control section 11 detects that the contents of the operations match, the display control section 18 displays a predicted image generated by the predicted image generating portion 25.

The image generating section 12 comprises: a request processing portion 21, which accepts a request for the generating of image data, requests a data list to the storage server 6 to obtain the data list, requests the storage server 6 to segment voxel data and to transfer the segmented voxel data to each image processing system which is the assignation of the segmented voxel data, and transmits a distributed volume rendering processing request to each image processing system; a calculation segmenting portion 22, which assigns a data load and a calculation load to each image processing system, considering the CPU utilization and the available memory of each image processing system; a distributed processing portion 23, which performs the distributed volume rendering process of the image processing system itself; an image coupling portion 24, which couples together all the distributed volume rendering image data transferred from the distributed processing portion 23 of the image processing system itself and from each image processing system, generates image data, and transfers the generated image data to the image memory 17 in response to each image data generating request; and a predicted image generating portion 25, which generates a predicted image that corresponds to an image of the target operation based on a history information that describes the contents of operations performed in the past.

Figure 2:
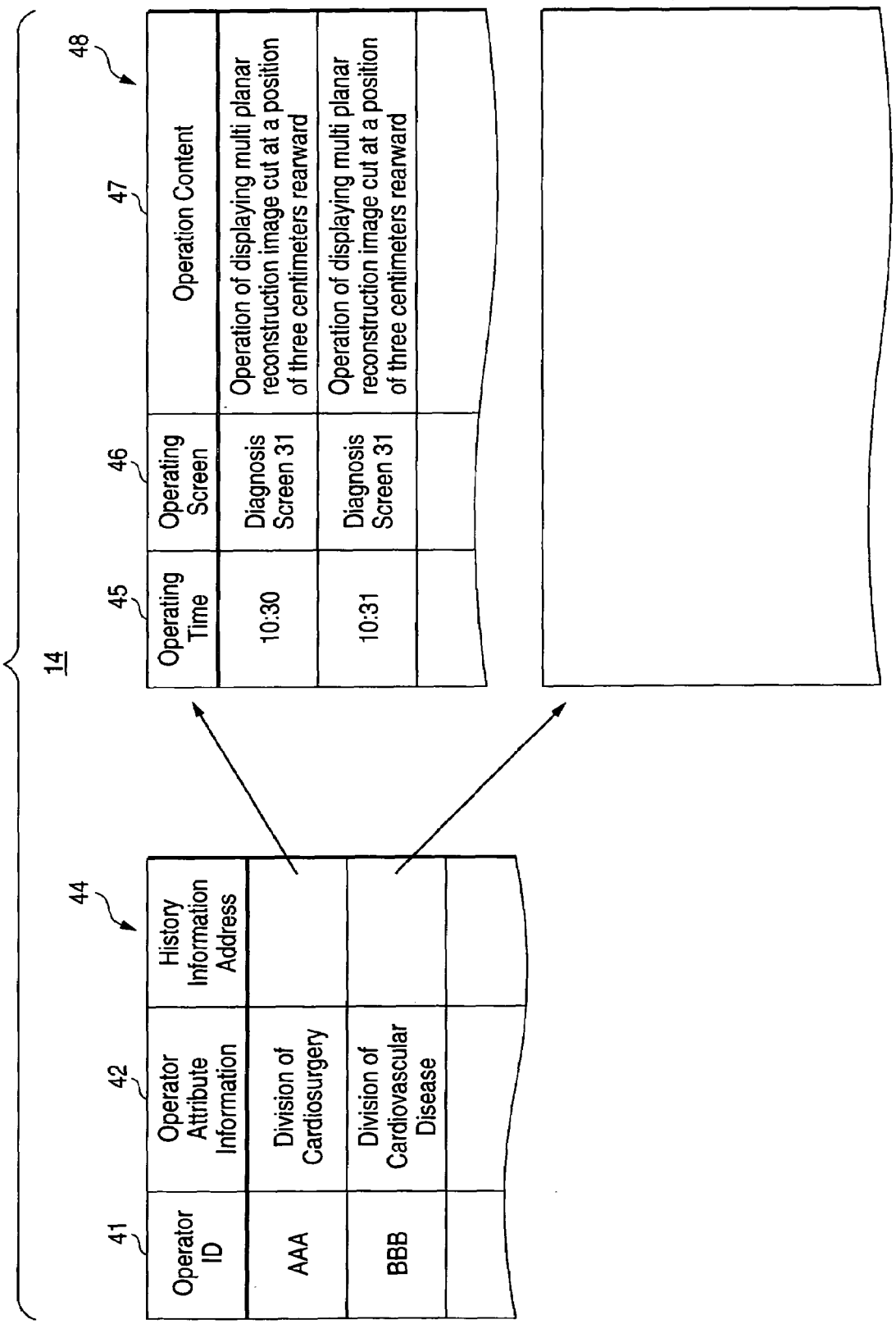
FIG. 2 is a diagram showing an example configuration for an operation history information storage section according to the embodiment of the invention.

The operating history information storage section 14 stores the contents of operations for every operator which are performed in the past. FIG. 2 is a diagram showing an example structure of the operating history information storage section in the embodiment of the invention. As is shown in FIG. 2, the operating history information storage section 14 provides operator information 44 which includes an operator ID 41 and an operator attribute information 42, and operating history information 48 which includes an operation time 45, an operating screen 46 that indicates a screen of a target operation, and operation content 47 for each operator information 44.

Figure 3:
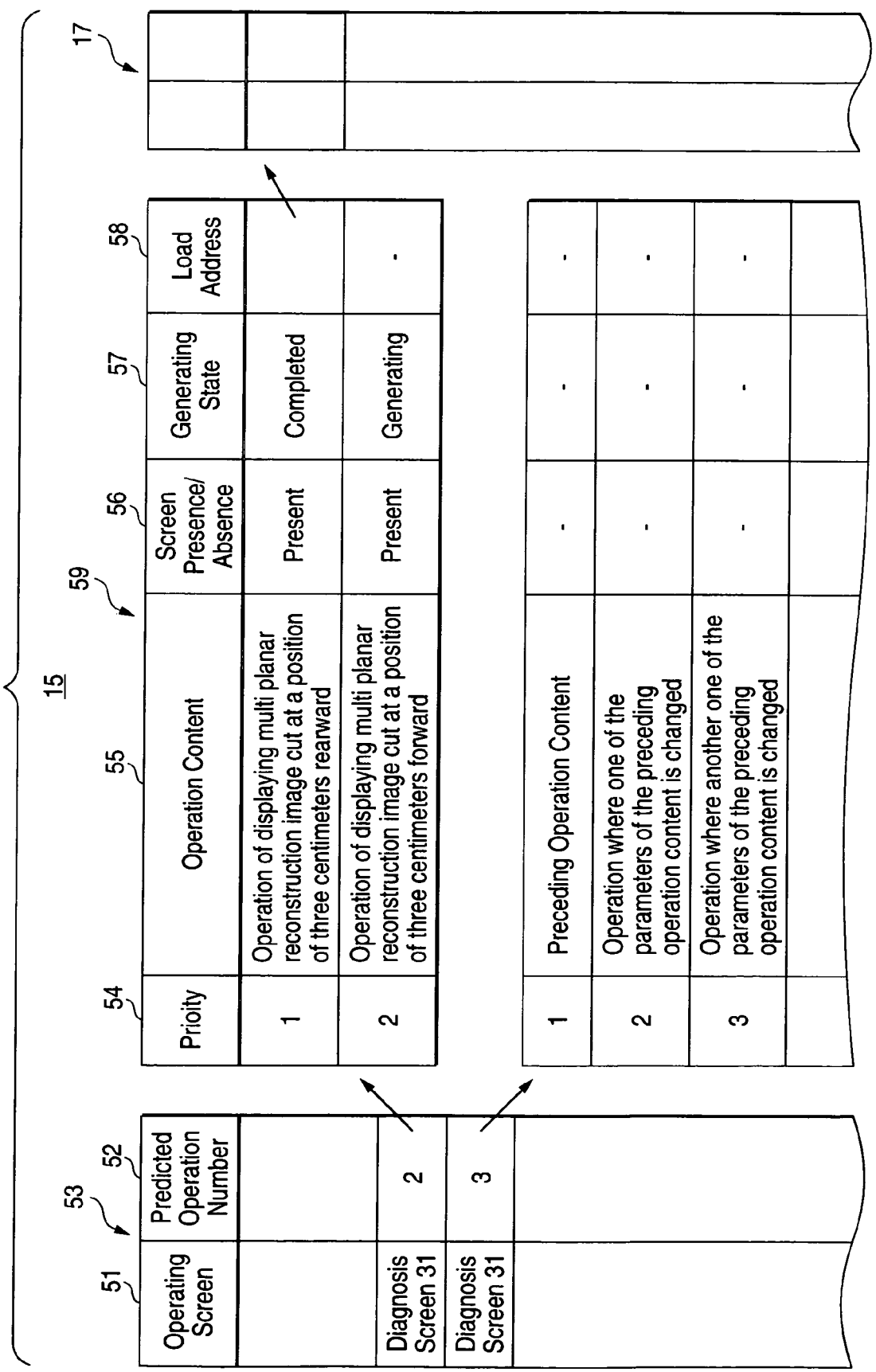
FIG. 3 is a diagram showing an example configuration for a predicted information storage section according to the embodiment of the invention.

The predicted information storage section 15 stores the contents of an operation predicted for each screen of the target operation, and addresses in the image memory 17 into which the predicted image data is loaded, generated based on the predicted operation contents. FIG. 3 is a diagram showing an example structure for the predicted information storage section 15 in the embodiment of the invention. As is shown in FIG. 3, the predicted information storage section 15 provides: a screen information 53, which includes an operating screen 51 that indicates the screen of the target operation, and a predicted operation number 52 that indicates the number of operations predicted for the operating screen 51; and a predicted information 59, which includes, for each screen information 53, a priority 54, an operation content 55, an image presence/absence 56 that indicates whether an image is displayed or not by the operation content 55, and when the image is displayed by the image presence/absence 56, a generating state 57 that indicates the state wherein a predicted image is generated, and a load address 58 that is the address of the image memory 17 into which generated predicted image data is loaded. The predicted information 59 is stored being set in the order of the priority for the number stored in the predicted operation number 52. Information which identifies an image for an operation is stored in the operating screen 51 and the operating screen 46 in the history information 48.

The number of data sets and the data type to be stored in the predicted information 59 can be freely selected and designed. When an operation that has high probability of being performed next is designated in the operating screen 51, the image display response of the entire image processing system 1 can be increased. The predicted operation number 52 may be either single or plural, and can be determined for each operating screen 51, considering the size of the image memory 17 provided in the image processing apparatus 3 and the probability that a predicted operation will be executed.

In the embodiment of the invention, it is assumed that the predicted operation number 52 is set to "2", wherein the operation content 55 of the first priority in the predicted information 59 is designated as a preceding operation, and the operation content 55 of the second priority is designated as an operation where one of the parameters of the preceding operation content is changed. Alternatively, it is assumed that the predicted operation number 52 is set to "3", wherein the operation content 55 of the first priority in the predicted information 59 is designated as a preceding operation, and the operation content 55 of the second priority and the third priority is designated as an operation where two of the parameters of the preceding operation contents are changed.

The operation content 55 in the predicted information 59 is not limited to the description above. The operation content may be designated as the operation content which is performed before two operations, not only the preceding operation. Moreover, the operation content may be designated as the most performed operation content, the operation content which is performed a predetermined number of times or more, or the operation content which combines these operation, among the operation content 47 in the past stored in the history information 48. The operation content 55 may be designated as some operations which are set in order according to the frequency of the performance of operation. Further, the operation content 55 may be designated as the partially changed operation content in the history information 48.

Since the operator attribute information 42 is included in the operating history information storage section 14, the operation content 55 of the predicted information 59 may be designated as a standard operation, which is generally performed by an operator in accordance with the operation attribute information 42, regardless of the history information 48. In this case, since different operation content 55 can be designated for each operator attribute information 42, multiple users can be coped with.

Based on the operation content 55 of the predicted information 59, the image generating section 12 requests to generate the image data by distributing the workload for the generating to the other image processing systems connected via a network. The request processing portion 21, the voxel data storage section 16 and the image memory 17 of the image generating section 12 are connected via the communication line 8 to the storage server 6 and the other image processing systems, whereby processing requests and data are transmitted and received mutually.

The storage server 6 stores medical image data for patients as voxel data, segments voxel data, and transfers the segmented voxel data to each image processing system which is the assignation of the segmented voxel data, according to an instruction received from the request processing portion 21 of the image generating section 12. Each image processing system is the same as the image processing system 1, and each comprises a distributed processing portion 23 and a voxel data storage section 16 which stores voxel data transferred from the storage server 6. Each image processing system performs assigned calculation processing for transferred voxel data, generates distributed volume rendering image data, and transfer the distributed volume rendering image data to the image coupling portion 24 of the image processing system 1 via the communication line 8.

Figure 4:
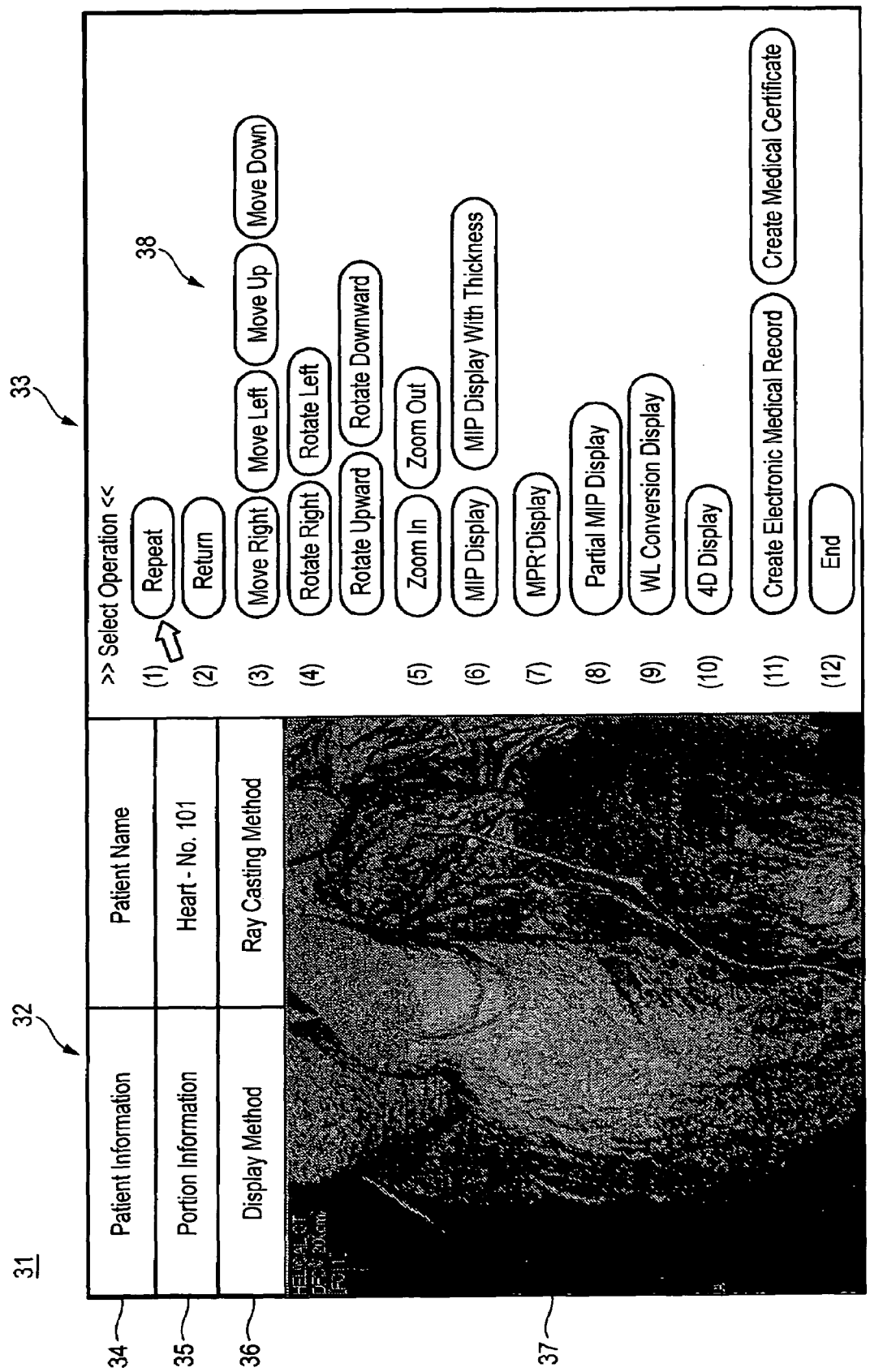
FIG. 4 is a diagram showing a first example of diagnosis screen displayed on a display device according to the embodiment of the invention.

FIG. 4 is a diagram showing a first example of a diagnosis screen displayed on the display device according to the embodiment of the invention. In FIG. 4, a diagnosis screen 31 includes an image information 32 that provides information related to a displayed image, and an operation menu 33 to select operation for the image. The image information 32 includes a patient information 34 such as a patient name and a patient ID, a portion information 35 which indicates a displayed portion, a display method 36 and a display window 37 which displays a volume rendering image. The display window 37 which is to be displayed is not limited to one; a plurality of display windows 37 may be provided to display multiple volume rendering images simultaneously.

The operation menu 33 presents an operation as a menu item 38, the operation being performed next for a volume rendering image displayed in the display window 37. For example, an operator selects a desired operation from the menu item 38, and inputs on the operation menu 33.

The menu item 38 which can be selected from the operation menu 33 on the diagnosis screen 31 is shown as the following.
(1) Repeat: repeat the preceding operation and display an image.
(2) Return: re-display the previously displayed image.
(3) Move right, Move left, Move up, Move down: move an image displayed on the display window 37.
(4) Rotate right, Rotate left, Rotate upward, Rotate downward: rotate a display angle and display an image.
(5) Zoom in, Zoom out: display a specific portion of an image by modifying the scale factor.
(6) MIP (Maximum Intensity Projection) display: display only the limited portion which is the brightest such as bones.
MIP display with thickness: display a MIP image with thickness.
(7) MPR (Multi Planar Reconstruction) display: display a two-dimensional image obtained by cutting a volume along an arbitrary cross-sectional surface. The cross-sectional surface can be designated as a flat surface or a curved surface.
(8) Partial MIP display: display an organ with thickness, while removing bones and other organs that can be distinguished by the level of brightness.
(9) WL (Window/Level) conversion display: display an image while converting the gray level for the display of the image.
(10) 4D (Dimension) display: move a three-dimensional image and display it as a moving picture which is continued in a time series.
(11) Create electronic medical record, Create medical certificate: write a volume rendering image displayed in the display window 37 into the individual format in order to obtain diagnosis information as a report.
(12) End: terminate image diagnosing.

When one of the (1) to (10) numbered menu items 38 on the operation menu 33 is selected and detailed operation content is input, image processing is performed and a volume rendering image is displayed. When one of the menu items 38 of the number (11) is selected, image processing is not performed, and a volume rendering image displayed on the display window 37 is stored in the frame of a predetermined format.

The menu item 38 selected on the operation menu 33 is stored in the operation content 47 of the history information 48 for each operator. The first priority of the predicted information 59 of the diagnosing screen 31 which is represented in a menu format stores the preceding operation that is selected according to the menu item 38. Further, the second priority stores the operation where one of the parameters of the preceding operation content that is selected according to the menu item 38 is changed.

Figure 5:
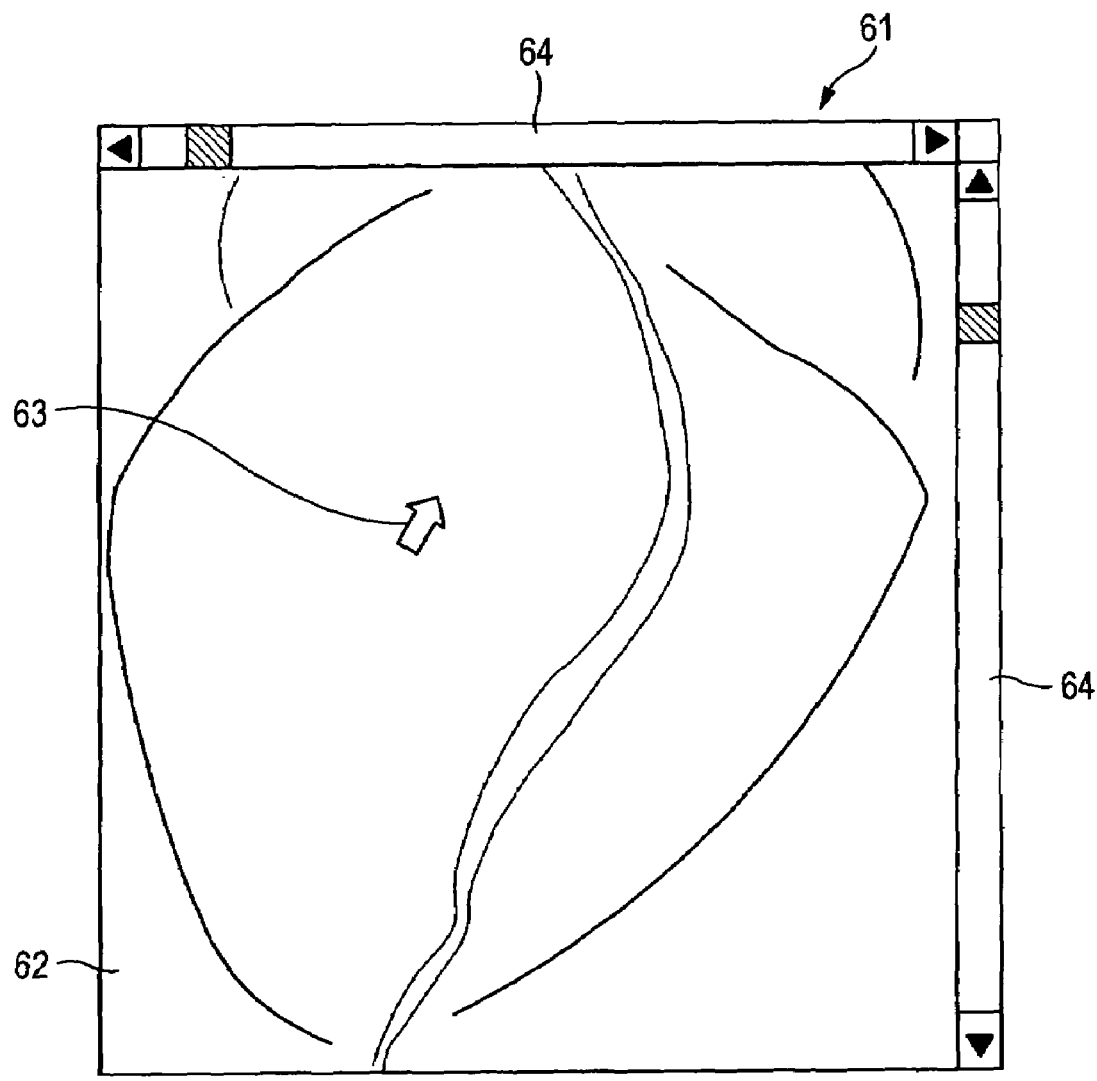
FIG. 5 is a diagram showing a second example of diagnosis screen according to the embodiment of the invention.

FIG. 5 is a diagram showing a second example of a diagnosing screen according to the embodiment of the invention. In FIG. 5, a diagnosis screen 61 indicates a display window 62 which displays a volume rendering image, a mouse pointer 63, and a slider 64 which moves the displayed portion to two edges of the display window 62 where a volume rendering image is displayed. On the diagnosis screen 61, a pan operation is performed wherein the slider 64 is moved by using the mouse pointer 63, or wherein the mouse pointer 63 is used to drag the volume rendering image in the display window 62 to display a portion of the image that was not previously visible. Furthermore, rotation processing by dragging is available when a mode is changed.

On the diagnosis screen 61, a direction and a distance that the slider 64 moved, or a direction and a distance that the mouse pointer 63 is dragged in the display window 62 is stored in the operation content 47 of the history information 48 for each operator. As shown in FIG. 3, the first priority of the predicted information 59 of the diagnosing screen 61 in which the pan operation is performed stores the preceding operation. Further, the second priority and the third priority store the operation content where two of the parameters of the preceding operation contents are changed.

Figure 6:
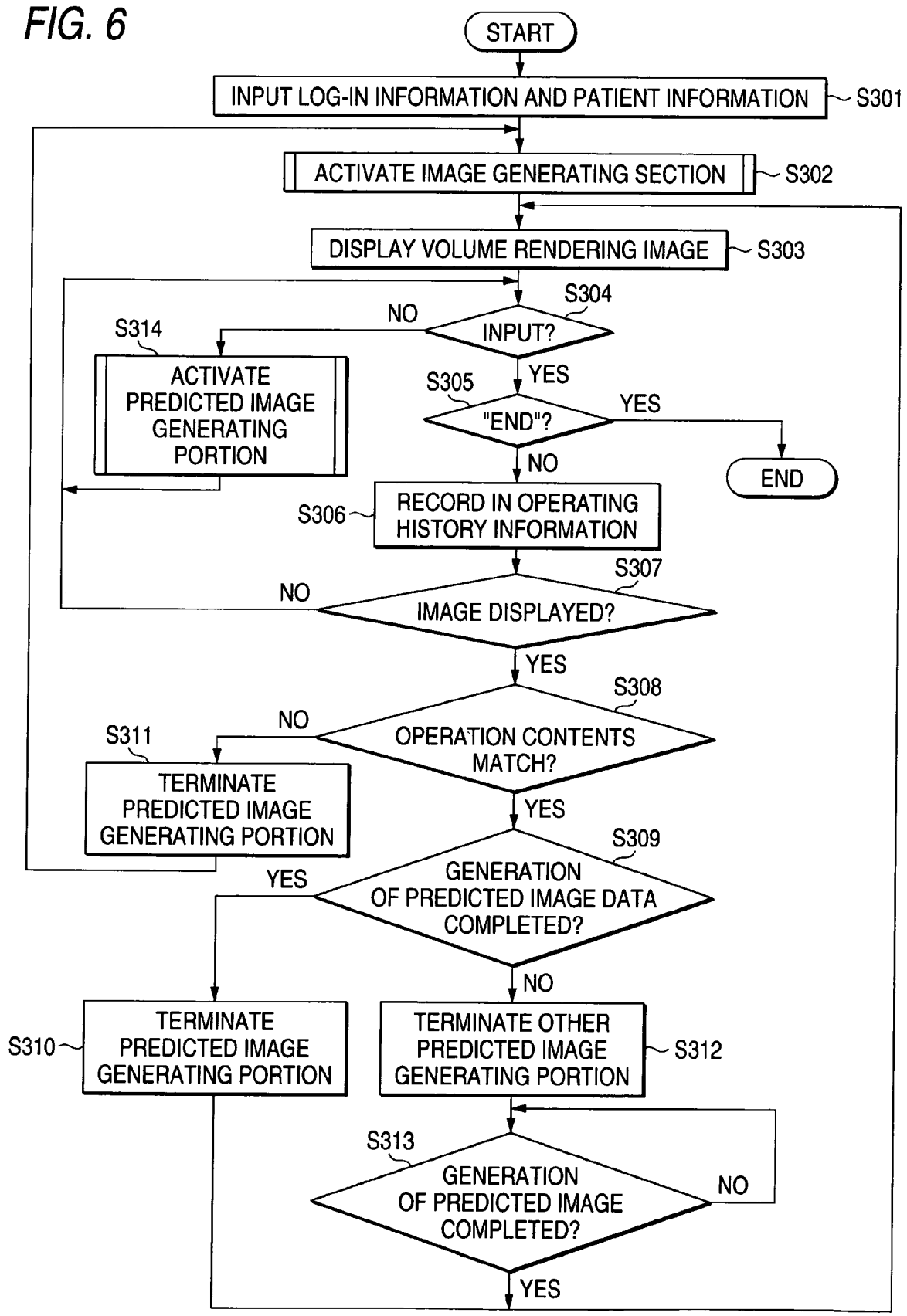
FIG. 6 is a flowchart for explaining the operation of the image processing apparatus according to the embodiment of the invention.
Figure 7:
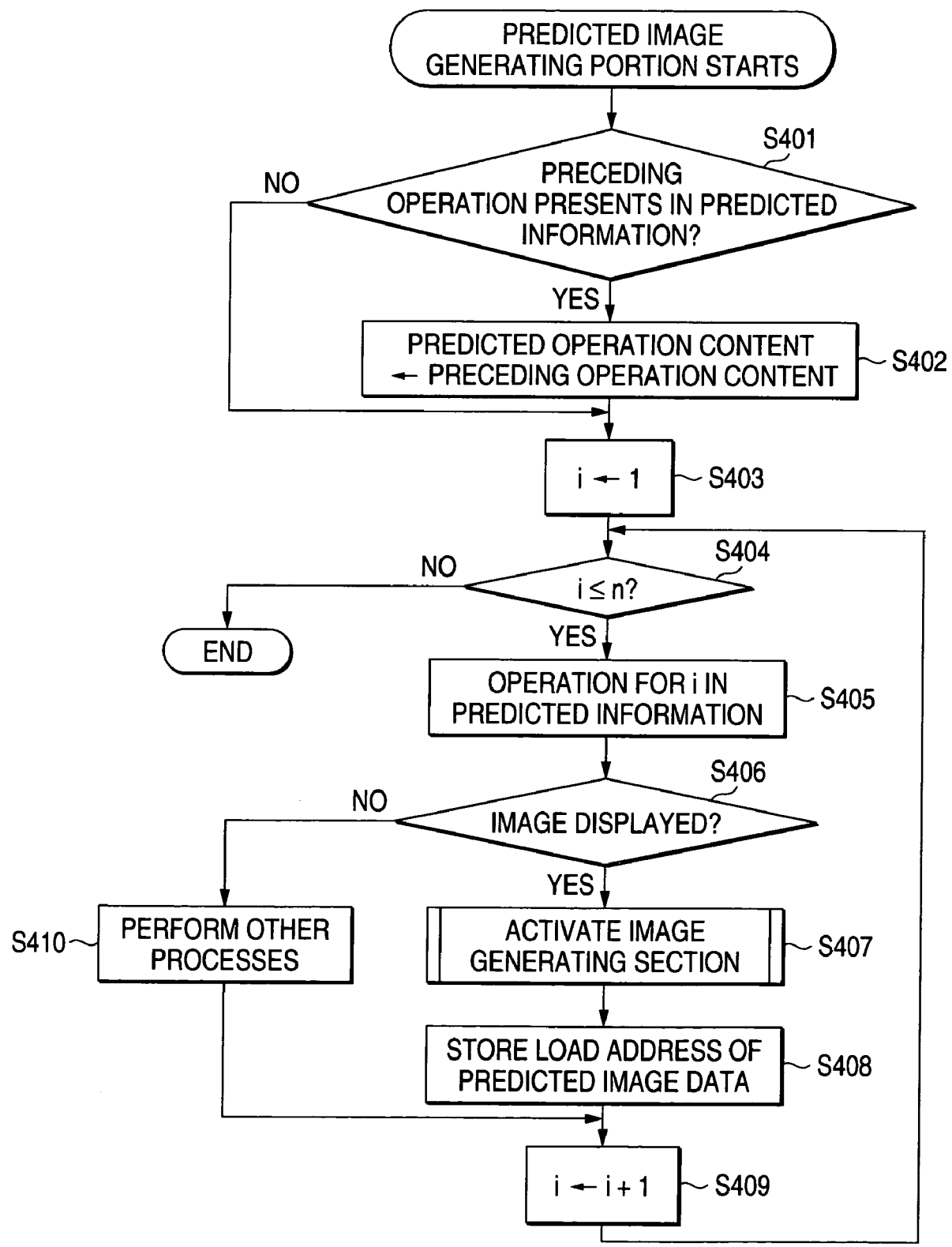
FIG. 7 is a flowchart showing the processing performed by a predicted image generator according to the embodiment of the invention.
Figure 8:
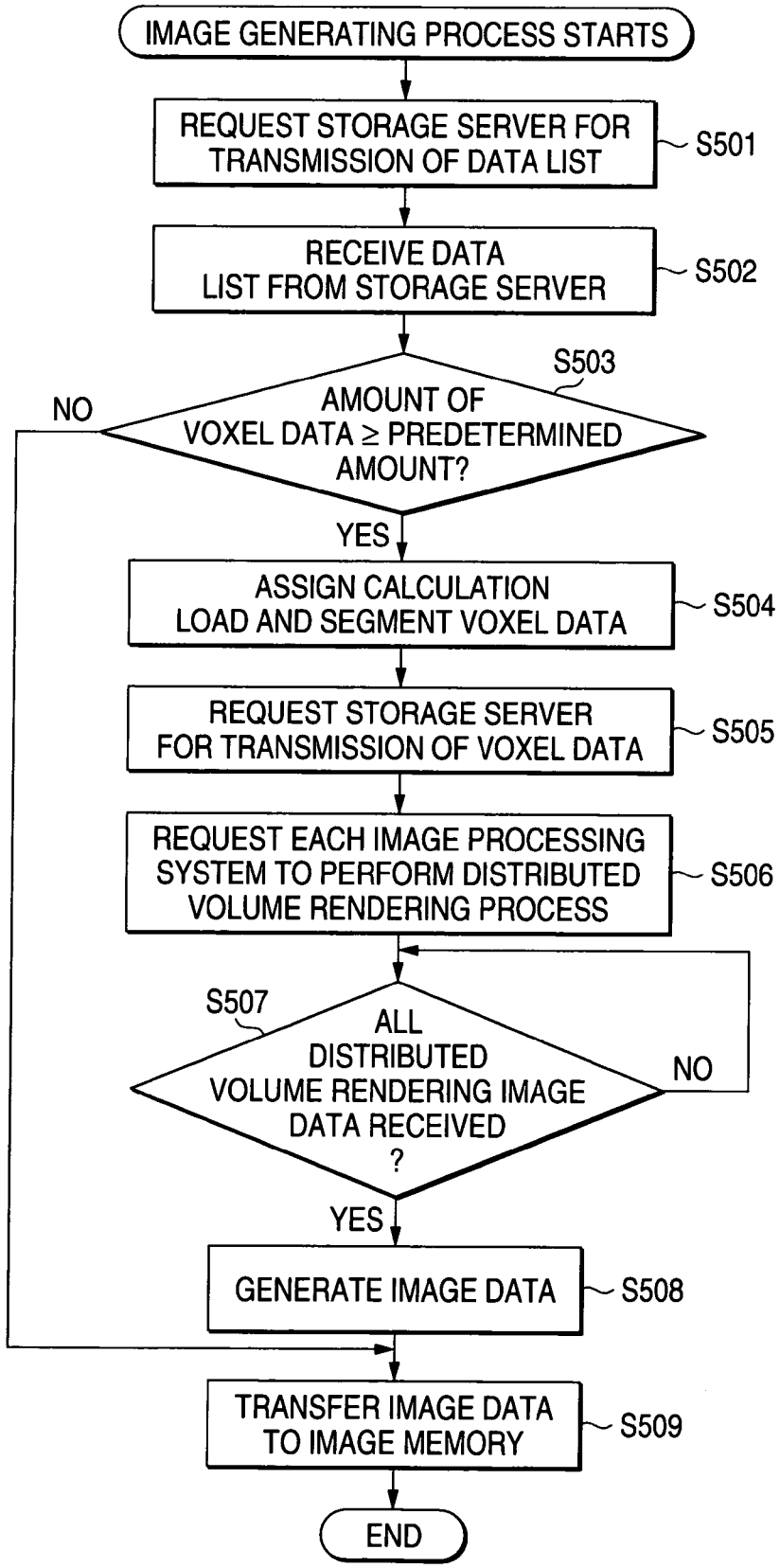
FIG. 8 is a flowchart showing the image generating processing according to the embodiment of the invention.
Figure 9A:
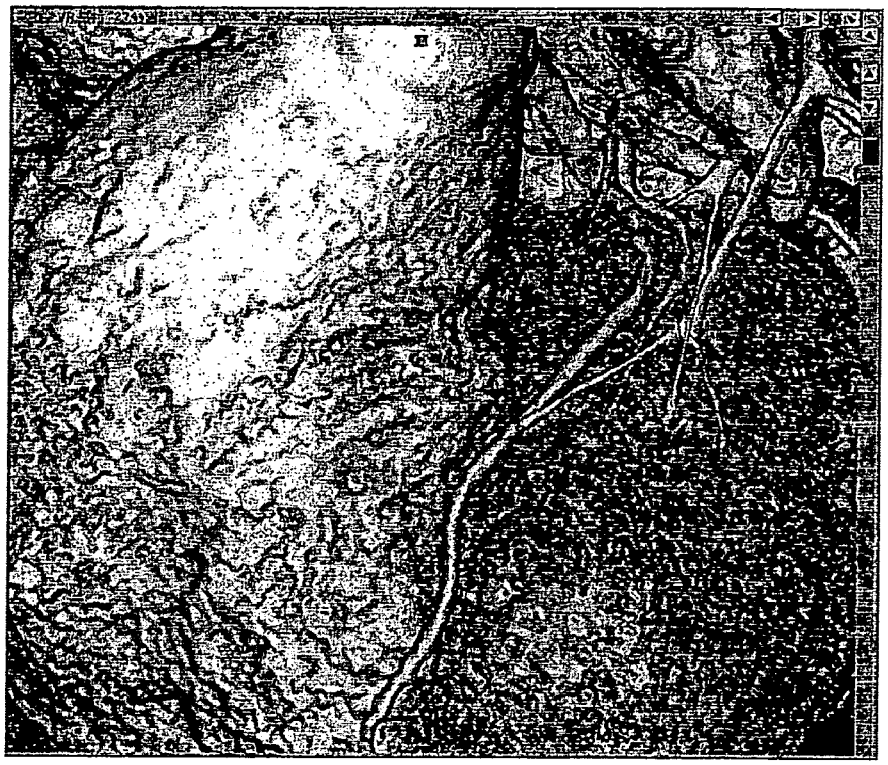
FIGS. 9A and 9B are diagrams showing examples of a screen display of a conventional image processing apparatus.
Figure 9B:
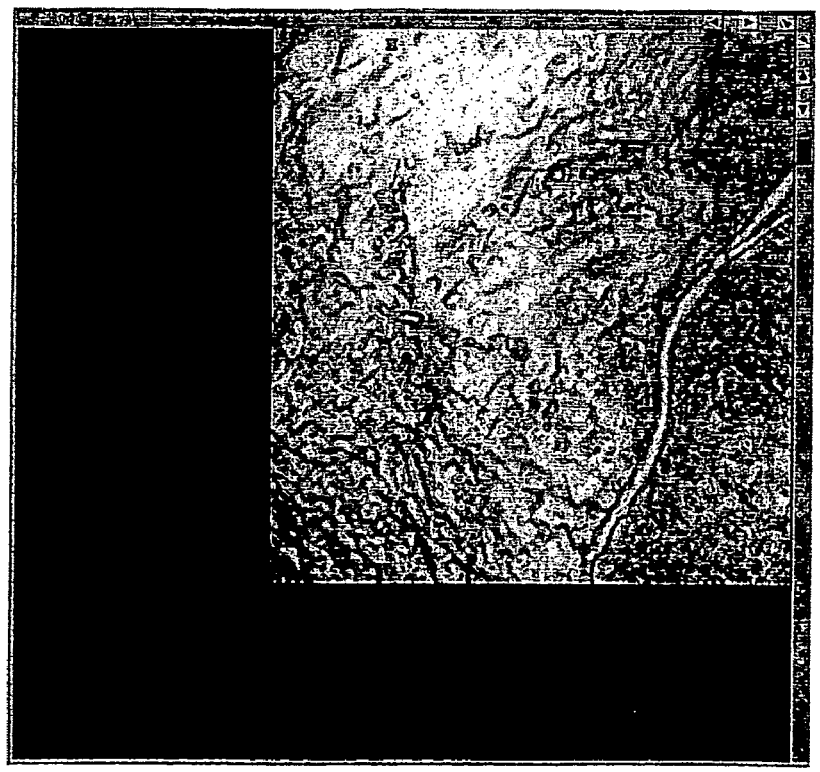

The operation of the thus arranged image processing apparatus 3 is described referring to FIGS. 6 to 8. FIG. 6 is a flowchart for explaining the operation of the image processing apparatus according to the embodiment of the invention. The operation of the image processing apparatus 3 is controlled mainly by the control section 11. As is shown in FIG. 6, at first, when an operator such as a doctor inputs a log-in information and a patient information for diagnosing from the input device 2 in step S301, the image generating section 12 is activated and a volume rendering image data of the designated patient is loaded into the image memory 17 in step S302. The display control section 18 displays the diagnosis screen where the volume rendering image is displayed in the display window 37 based on the image memory 17, on the display device 4 in step S303.

When an operation is input from the diagnosis screen, which represents YES at step S304, and when the operation is not "End", which represents NO at step S305, the operation content is stored in the operation content 47 of the history information 48 in step S306.

When an image is displayed as a result of the input operation, which represents YES at step S307, it is detected that whether the input operation content match with the operation content in the operation contents 55 of the predicted information 59 that is generated in the operating screen 51 same as the displayed screen. When the operation content matches, which represents YES at step S308, and when generating processing is already completed by the predicted image generating portion and the generating state 57 of the predicted information 59 is completed, which represents YES at step S309, the predicted image generating portion 25 terminates the operation currently being performed in step S310. Program control then returns to step S303, and displays predicted image data that is loaded in the image memory 17 by the load address 58, in the display window 37 in step S303.

When, in step S307, an image to be displayed does not exist as a result of the input operation, which represents NO at step S307, program control returns to step S304 and waits for the next input. When, as a result of the input operation, an image to be displayed exists, which represents YES at step S307, and when the operation input at step S304 does not match the operation content in the operation contents 55 of the predicted information 59, which represents NO at step S308, the predicted image generating portion 25 terminates the currently performed operation in step S311. Then, program control returns to step S302, and the image generating section 12 generates image data to be displayed, in accordance with the input operation in step S302. The process in step S302 is the same process as the one performed by the conventional image processing apparatus.

When an image is displayed as a result of the input operation, which represents YES at step S307, and when the matching of the operation input at step S304 and the operation content 55 of the predicted information 59 is detected, which represents YES at step S308, and when the predicted image generating portion 25 is not yet completed the process for generating predicted image data to be displayed, which represents NO at step S309, the predicted image generating portion 25 terminates another operation currently being performed in step S312. Thereafter, when the generating process of the predicted image data is completed, which represents YES at step S313, program control returns to S303, and displays predicted image data that is loaded in the image memory 17 by the load address 58 of the predicted information 59, in the display window 37 in step S303.

When an input does not exist at step S304, which represents NO at step S304, the predicted image generating portion 25 is activated and generates predicted image data based on the predicted information 59 in step S314. When the image processing apparatus 3 performs another process in parallel, and when an input does not exist at step S304, which represents NO at step S304, and when the CPU utilization of the image processing system 1 is a predetermined value or smaller, the predicted image generating portion 25 may be activated at step S314.

FIG. 7 is a flowchart showing the operation of the predicted image generating portion according to the embodiment of the invention. As is shown in FIG. 7, the predicted image generating portion 25 generates predicted image data based on the operation content 55 of the predicted information 59 which is generated in the operating screen 51 that is same as the displayed image. Since the predicted information 59 is arranged in descending order by the priority, predicted image data is generated in accordance with the priority.

Assuming that n sets of predicted information 59 is stored in the predicted operation number 52 as n, when an unknown element, such as the preceding operation content, is included in the operation content 55 of the n sets of predicted information 59, which represents YES at step S401, the predicted information 59 is determined in step S402, by, for example, substituting the preceding operation content 47 and stored at the head of the history information 48 provided for each operator, for the operation content 55 of the predicted information 59. If all the operation contents 55 of the predicted information 59 are determined, which represents NO at step S401, the process at step S402 does not need to be performed.

Assigning 1 for i in step s4O3, and when i is equal to or smaller than n, which represents YES at step S404, the operating condition is designated in accordance with the operation content 55 for i which is stored in the predicted information 59 in step S405.

When the operation content 55 for i is an operation which displays an image, which represents YES at step S406, the predicted image data of a volume rendering image that is generated in the image generating section 12 is loaded into the image memory 17 in step S407. Then the address of the predicted image data in the image memory 17 is stored in the load address 58 of the predicted information 59 in step S408, and assuming i=i+1 in step S409, program control returns to step S404. The process from step S405 to step S409 is repeated until the process for all the operation contents 55 included in the predicted information 59 are completed, which represents NO at step S404, and all of the predicted image data corresponding to an image of the target operation are generated and loaded into the image memory 17 based on each operation content 55.

When the operation content 55 for i is not the operation content which displays an image, which represents NO at step S406, another process is performed in step S410 such as the writing process of data to an electronic medical record or the loading process of data.

When the process for all the operation contents 55 of the predicted information 59 is completed in step S404, which represents YES at step S404, the image data generating process is terminated.

FIG. 8 is a flowchart showing the image generating process according to the embodiment of the invention. As shown in FIG. 8, upon receiving an image generating request, the request processing portion 21 of the image generating section 12 requests the storage server 6 to transmit a data list for the requested image in step S501, and receives the data list in step S502. The data list includes information indicating the amount of voxel data for the medical image.

When the amount of voxel data is equal to or greater than a predetermined value, which represents YES at step S503, the distributed processing portion 23 assigns the calculation load to each image processing system that handles the distributed process based on the calculation resource usage state information such as the amount of voxel data, and the CPU utilization and available memory of each image processing system, and determines the segmenting ratio of the voxel data in step S504.

The request processing portion 21 requests the storage server 6 to transmit voxel data to each image processing system based on the segmenting ratio of the voxel data in step S505. Then, the request processing portion 21 requests each image processing system to perform a distributed volume rendering process equivalent to the assigned calculation load in step S506.

Upon receiving the transmission request of the voxel data, the storage server 6 segments the voxel data in accordance with the instruction, and transmits the segmented voxel data segments to the voxel data storage sections 16 of each image processing system which is the assignation of the segmented voxel data.

The distributed processing portion in each image processing system performs an assigned calculation process for the assigned data that is stored in the voxel data storage section 16, and performs the distributed volume rendering process. Thereafter, the distributed volume rendering image data processed in each image processing system is transferred to the image coupling portion 24 of the image processing apparatus 3 via the communication line 8.

When the image coupling portion 24 of the image generating section 12 receives the distributed volume rendering image data from the distributed processing portion 23 of the self image processing system, and all the distributed volume rendering image data transferred from the other image processing systems, which represents YES at step S507, the image coupling portion 24 generates image data by coupling all the distributed volume rendering image data together in step S508. Then, the coupling portion 24 loads the generated image data into the image memory 17 for each image generating request in step S509, and the processing is terminated.

When the diagnosis screen 31 shown in FIG. 4 is displayed, the first priority of the predicted information stores the preceding operation, and the second priority stores the operation where one of the parameters of the preceding operation content is changed. In this case, the parameter to be changed may be the parameter which is changed by the operator before the preceding operation, in the history information 48. The parameter to be changed may be selected from the most performed operation contents among the operation contents 47 in the past.

The processing that is performed immediately after one of the following operations is selected and an image is displayed on the diagnosis screen 31 is now will be described.

(1) Move right, Move left, Move upward, Move downward (pan operation performed by manipulating a button): It is assumed that the operation content 55 of the first priority of the predicted information 59 is designated as the same operation as the preceding operation, and that the operation content 55 of the second priority is designated as an operation obtained by changing the moving distance in the preceding operation. When an operator is manipulating a button of "Move right", "Move left", "Move upward" or "Move downward", while changing the moving distance, and viewing an image, the predicted image generating portion 25 generates the predicted image data when the same operation is performed as the preceding operation based on the operation content 55 of the first priority of the predicted information 59, also generates the predicted image data when the operation where the moving distance of the preceding operation is changed based on the operation content 55 of the second priority. Then the predicted image data is loaded into the image memory 17. Through this process, when the operator sequentially performs the same moving operation, or performs the operation with a slightly different moving distance, as the predicted image that is generated in advance can be displayed, a volume rendering image can be promptly displayed in consonance with the moving operation.

(2) Rotate right, Rotate left, Rotate upward, Rotate downward: It is assumed that the operation content 55 of the first priority of the predicted information 59 is designated as the same operation as the preceding operation, and that the operation content 55 of the second priority is designated as an operation obtained by changing the rotating direction of the preceding operation oppositely. When an operator is manipulating a button of "Rotate right", "Rotate left", "Rotate upward" or "Rotate downward", while changing the rotating direction, and viewing an image, the predicted image generating portion 25 generates the predicted image data when the same operation is performed as the preceding operation based on the operation content 55 of the first priority of the predicted information 59, also generates the predicted image data when the operation where the rotating direction of the preceding operation is changed oppositely based on the operation content 55 of the second priority. Then the predicted image data is loaded into the image memory 17. Through this processing, when the operator performs the same operation, or performs the operation of turning the rotation direction back, as the predicted image that is generated in advance can be displayed, a volume rendering image can be promptly displayed in consonance with the rotating operation.

(3) Zoom in, Zoom out: It is assumed that the operation content 55 of the first priority of the predicted information 59 is designated as the same operation as the preceding operation, and that the operation content 55 of the second priority is designated as an operation obtained by modifying the scale factor of the preceding operation. When an operator is manipulating a button of "Zoom in" or "Zoom out", while modifying the scale factor, and viewing an image, the predicted image generating portion 25 generates the predicted image data when the same operation is performed as the preceding operation based on the operation content 55 of the first priority of the predicted information 59, also generates the predicted image data when the operation where the scale factor of the preceding operation is modified based on the operation content 55 of the second priority. Then the predicted image data is loaded into the image memory 17. Through this processing, when the operator performs the same operation, or performs the operation where the scale factor is modified, as the predicted image that is generated in advance can be displayed, a volume rendering image can be promptly displayed in consonance with the scale factor modification.

(4) MPR display: It is assumed that the operation content 55 of the first priority of the predicted information 59 is designated as the same operation as the preceding operation, and that the operation content 55 of the second priority is designated as an operation obtained by changing the preceding operation reversely. For example, assuming that an operation of displaying the MPR image which is cut at a position of three centimeters rearward is performed immediately before, the operation content 55 of the first priority of the predicted information 59 stores an operation of displaying a MPR image obtained by shifting the cutting position three centimeters reward. The operation content 55 of the second priority stores an operation of displaying a MPR image obtained by shifting the cutting position three centimeters forward, with the change of the direction which is one parameter of the operation content. When the operator is viewing the MPR image obtained by shifting the cutting position three centimeters rearward, the predicted image generating portion 25 generates the predicted image data of the MPR image obtained by shifting the cutting position further three centimeters rearward, based on the operation content 55 of the first priority of the predicted information 59. Also, the predicted image generating portion 25 generates the predicted image data of the MPR image obtained by shifting the cutting position three centimeters forward with the change of the direction of the preceding operation based on the operation content 55 of the second priority. Then the predicted image data is loaded into the image memory 17. Through this processing, when the operator performs the same operation, or performs the operation of shifting the cutting position to the opposite direction, as the predicted image that is generated in advance can be displayed, a volume rendering image can be promptly displayed in consonance with the MPR display operation.

(5) 4D display: The operation content 55 of the first priority of the predicted information 59 indicates a request to display a volume rendering image obtained by forwarding a certain number of frames, and the operation content 55 of the second priority indicates a request to display a volume rendering image obtained by setting a certain number of frames backward. When "4D display" is selected, as an operation is initiated sequentially that requests the display of volume rendering image obtained by forwarding a certain number of frames, the predicted image generating portion 25 sequentially generates the predicted image data of the volume rendering image of a certain frame based on the operation content 55 of the first priority and the operation content 55 of the second priority of the predicted information. Then the predicted image data is loaded into the image memory 17. Through this processing, until the generating process of the new image, which is changed by the operator moving the positions of images to be displayed, is completed, as the predicted image that is generated in advance can be displayed, moving pictures of the volume rendering images can be smoothly displayed in accordance with the 4D display operation.

Some example operations that can be obtained by changing a one-dimensional parameter are a process that employs a color look-up transformation function, a WW/WL transformation process, and a process that employs an opacity function. These processes can be performed in the same manner as the above described display of the image types.

(6) Color look-up transformation function: A color look-up transformation function is a transformation function that allocates a color represented by three parameters of R, G and B, to a voxel value represented as a scaler value by volume rendering process. The color look-up transformation function is generally obtained by a section continuous function, a spline function or a free curve function, each of which is allocated to R, G, and B respectively, and for example, the color obtained by volume rendering can be changed by altering the parameter for the section continuous function. The color look-up transformation enables to obtain a monochromatic image transformation, and in this case, an allocated luminance is provided for a voxel value. One example form is a WW/WL transformation.

(7) Opacity function: An opacity function is a transformation function for allocating an opacity level to a voxel value that is represented as a scaler value by volume rendering process. The opacity function is represented by a section continuous function, a spline function or a free curve function. For example, when a volume rendering image represents abone, volume rendering is performed such that the bone gradually becomes transparent as the parameter for the opacity level is reduced.

(8) Generate electronic medical record: When the operation content of "generate electronic medical record" is stored as the operation content 55 of the predicted information 59, during a period wherein a new volume rendering image is displayed and the next entry by an operator is being waited for, the predicted image generating portion 25 performs the process that stores the new displayed volume rendering image to the electronic medical record. Therefore, the next operation which writes a volume rendering image of an affected part into an electronic medical record is smoothly performed during diagnosing.

Further, when the loading of data is stored as the operation content 55 of the predicted information 59, the predicted image generating portion 25 performs the process of loading the data during a period wherein the next entry by the operator is being waited for. Therefore, when the previously loaded data, or a diagnosis image newly obtained by a CT apparatus or other data concerning a patient currently being browsed, is designated in advance as data to be loaded, as a data for the patient of the next target operation is automatically loaded, the operator does not need to wait for patient data to be read out.

(9) Pan process: An explanation will now be given for a process performed immediately after a pan process is instructed on the diagnosis screen 31 by mouse dragging. It is assumed that the first priority of the operation content 55 of the predicted information 59 is a pan operation. Based on the fact that the image obtained as a result of a pan operation is an image which represents a portion that does not fit on the screen compared to the volume rendering image currently displayed on the screen, the image that comprises a predicted image by calculating an image having a portion that does not fit in the screen can be generated. Then the image having a portion that does not fit in the screen is loaded in the image memory 17. As a predicted image generated in advance can be displayed the next time when the operator performs the pan process, a volume rendering image can be promptly displayed for any pan process. Hereinafter, the pan process performed by mouse dragging is specifically described.

An explanation will be given for the process performed immediately after the pan process for displaying a volume rendering image having a portion that is previously hidden by moving the slider 64, or dragging the mouse pointer 63 in the display window 62, on the diagnosis screen 61 in FIG. 5. The moving direction and the moving distance of the slider 64, or the moving direction and the moving distance of the mouse pointer 62, are stored in the operation content 47 of the history information 48 for each operator. As shown in FIG. 3, the first priority in the predicted information 59 stores an operation content of a preceding operation, and the second priority and the third priority store operations where two of the parameters of the preceding operation contents are changed.

For example, when the operation of pointing the mouse pointer 63 on the volume rendering image in the display window 62 and dragging the volume rendering image to a direction of 30 degrees diagonally upward right by three centimeters is performed, and the volume rendering image is displayed, the preceding operation in the operation content 47 of the history information 48 stores the operation for displaying the volume rendering image which is moved to a direction of 30 degrees diagonally upward right by three centimeters. Similarly, the first priority of the predicted information 59 stores the operation for displaying the volume rendering image which is moved to a direction of 30 degrees diagonally upward right by three centimeters. Further, the second priority stores the operation for displaying the volume rendering image which is moved to a direction of horizontally right by three centimeters. Further, the third priority stores the operation for displaying the volume rendering image which is moved to a direction of vertically upward by three centimeters.

While an operator is viewing the volume rendering image which is moved to a direction of diagonally upward right by three centimeters, the predicted image generating portion 25 generates the predicted image data of the volume rendering image which is moved to a direction of diagonally upward right by three centimeters further, based on the operation content 55 of the first priority of the predicted information 59; generates the predicted image data of the volume rendering image which is moved to a direction of horizontally right by three centimeters, based on the operation content 55 of the second priority; and generates the predicted image data of the volume rendering image which is moved to a direction of vertically upward by three centimeters, based on the operation content 55 of the third priority. These predicted image data are stored in the image memory 17. Through this processing, when the operation is slightly different from the previous operation, as an image can be promptly displayed by the predicted image data generated in advance, a volume rendering image which corresponds to pan operation can be promptly displayed.

(10) Rotation process by mouse dragging: An explanation will now be given for the process performed immediately after the rotation process by mouse dragging is instructed on the diagnosis screen 31. The history information for the rotation process is obtained by six parameters: three parameters representing the coordinate of the rotating center, two parameters representing the rotating direction, and one parameter representing the rotational amount. By fixing the three parameters that represent the coordinate of the rotation center and the two parameters that represent the rotating direction for the history information which is obtained by six-dimensional degrees of freedom in order to reduce the number of dimensions to a single dimension, the predicted information 59 can be generated. While an operator is viewing an image, the predicted image generating portion 25 generates the predicted image data based on the operation content 55 of the first priority of the predicted information 59, and loads the predicted image data into the image memory 17. Through this process, when the operator continues to perform the operation of rotating the image in the same direction at the same rotation center coordinate, as the predicted image generated in advance can be displayed, a volume rendering image can be quickly displayed in accordance with the rotation operation.

So far as the calculation resource permits, it is preferable that multiple predicted images are generated as predicted image data.

The case during which a predicted image is generated based on history information is explained above. However, there is another case wherein generating of a predicted image is also possible based on the current operating state, not only using the previous operation as history. For example, when the current operating state is "MPR display", the operation for changing the MPR cutting plane is a typical operation, therefore there is an adequate reason to be regarded as a predicted operation. Further, when the current operating state is a "VE (Virtual Endoscopy) display", the flying-through operation for moving a VE camera forward and backward, such as an operation for moving the VE camera along the path of an intestine, is a typical operation, therefore there is an adequate reason to be regarded as a predicted operation. It is effective to generate a predicted image according to each current operating state.

As an extension of the embodiment, an operation regarded as the operation contents in the predicted information can be a transition generating to a relevant operating state from a current operating state, such as changing the position of a camera on the path during the VE flying-through operation, the position of a cutting plane during the region extraction process with the cutting by a plane, the radius of a sphere during the region extraction process with the cutting by a sphere, a threshold value during the region extraction process using the threshold value, and other parameters required for the region extraction process, for example, extracting a cerebral aneurysm while editing the image of a brain.

According to the embodiment described above, the following effects can be obtained.

(1) Since the predicted image generating portion 25 is provided that generates the predicted image corresponding to an image of a target operation based on the predicted information, an image data generated in advance can be displayed without generating an image for each operation. Therefore, an image consonant with the contents of the operation can be promptly displayed.

(2) Since the operation of an operator is stored in the history information 48 for every input, the predicted information 59 is generated based on the operation content 47 of the history information 48, and a predicted image is generated in accordance with the predicted information 59, multiple users can be coped with.

(3) The operation content 55 of the predicted information 59 is generated by changing one parameter of the operation content 47 of the history information 48, and a predicted image is also generated based on the changed parameter. Thus, the rate for the quick display of the image can be increased.

(4) The operation content 55 of the predicted information 59 is generated by changing two parameters of the operation content 47 of the history information 48, and a predicted image is also generated based on the changed parameters. Therefore, even when the next operation is hardly the same operation as the preceding operation as a pan processing, an image can be promptly displayed by using the predicted image, so long as the current operation is similar to the previous one.

(5) Since the predicted image data is generated while waiting for the next input, the calculation resource can be effectively utilized.

(6) Since a plurality of predicted image data are generated in advance based the predicted information, the probability that an image is displayed in accordance with an input operation content can be increased.

(7) Since the calculation load of volume rendering process is distributed to other image processing systems via a network, the load imposed by the generating of image data can be reduced, and the processing time can also be reduced.

According to the present invention, since the predicted image generating section is provided that generates a predicted image in consonance with an image of a target operation based on a predicted information, an image that is generated in advance can be displayed without generating an image for each operation. Therefore, an image consonant with the operation content can be promptly displayed, and the present invention can be effectively employed for apparatuses, for example, other than the apparatuses used in a medical field, an electronic microscope, and other apparatuses that obtain image data by performing a complicated calculation in real time, and display an image, such as an apparatus used for weather chart maps, geologic maps like oil survey maps, atlases and nondestructive testing.

According to the present invention, since a predicted image consonant with an image of a target operation is generated based on a predicted information, an image which is generated in advance can be displayed without generating an image for each operation. As a result, an image corresponding to the operation contents can be promptly displayed.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An image processing apparatus comprising:
a predicted information storage section for storing a predicted information indicating operation contents which are predicted for an image of a target operation;
a predicted image generating section for generating a predicted image based on the predicted information so as to be corresponding to the image of the target operation; and
an image display control section for displaying an image based on said generated predicted image when operation contents of an input operation match those of said predicted information,
wherein the predicted image generating section generates a volume rendering image that is obtained by a pan operation which is determined by changing a two-dimensional parameter, when the preceding operation content is a pan operation that moves the target volume rendering image two-dimensionally parallel to a projection plane, without changing the projection angle.

2. An image processing apparatus according to claim 1, wherein the predicted information is generated based on a current operating state.

3. An image processing apparatus according to claim 1, wherein the predicted information is an operation information obtained by changing the two-dimensional parameter; and wherein the predicted image generating section generates the predicted image based on the operation information obtained by changing the two-dimensional parameter.

4. An image processing apparatus according to claim 3, wherein the two dimensional parameter of the operation information which is obtained by changing the two-dimensional parameter is used for determining a vertical or horizontal relative position of a pan operation.

5. An image processing apparatus according to claim 1, wherein the predicted image generating section generates the predicted image by distributing a calculation load, requiring for generating the predicted image, to a plurality of image processing apparatuses connected via a network.

6. An image processing apparatus according to claim 1, which performs a volume rendering process based on a voxel data.

7. An image processing apparatus according to claim 1, wherein the predicted image generating section generates the predicted image by distributing a calculation load, requiring for generating the predicted image, to a plurality of image processing apparatuses connected via a network.

8. An image processing apparatus comprising:
a predicted information storage section for storing a predicted information indicating operation contents which are predicted for an image of a target operation;
a predicted image generating section for generating a predicted image based on the predicted information so as to be corresponding to the image of the target operation; and
an image display control section for displaying an image based on said generated predicted image when it is determined that operation contents of an user input operation match those of said predicted information,
wherein the predicted information is an operation information obtained by automatically changing a selected one-dimensional parameter, and further wherein the predicted image generating section generates the predicted image based on the operation information obtained by automatically changing the selected one-dimensional parameter, wherein, when a type of the image of the target operation is a multi planar reconstruction image, the one-dimensional parameter of the operation information which is obtained by changing the selected one-dimensional parameter is a parameter for a cut position of a displayed slice of a multi planar reconstruction image.

9. An image processing apparatus comprising:
a predicted information storage section for storing a predicted information indicating operation contents which are predicted for an image of a target operation;
a predicted image generating section for generating a predicted image based on the predicted information so as to be corresponding to the image of the target operation; and
an image display control section for displaying an image based on said generated predicted image when it is determined that operation contents of an user input operation match those of said predicted information,
wherein the predicted information is an operation information obtained by automatically changing a selected one-dimensional parameter, and further wherein the predicted image generating section generates the predicted image based on the operation information obtained by automatically changing the selected one-dimensional parameter, wherein, when a type of the image of the target position is a moving picture, the one-dimensional parameter of the operation information which is obtained by changing the selected one-dimensional parameter is used for determining a display frame for the moving picture.

10. An image processing apparatus comprising:
a predicted information storage section for storing a predicted information indicating operation contents which are predicted for an image of a target operation;
a predicted image generating section for generating a predicted image based on the predicted information so as to be corresponding to the image of the target operation; and
an image display control section for displaying an image based on said generated predicted image when operation contents of an input operation match those of said predicted information,
wherein the predicted information is an operation information obtained by changing a selected one-dimensional parameter, and further wherein the predicted image generating section generates the predicted image based on the operation information obtained by changing the selected one-dimensional parameter, and wherein the one-dimensional parameter of the operation information which is obtained by changing the one-dimensional parameter is a look-up table parameter, wherein the one-dimensional parameter of the operation information which is obtained by changing the one-dimensional parameter is one of the parameters for defining a color look-up transformation function.

11. An image processing apparatus comprising:
a predicted information storage section for storing a predicted information indicating operation contents which are predicted for an image of a target operation;
a predicted image generating section for generating a predicted image based on the predicted information so as to be corresponding to the image of the target operation; and
an image display control section for displaying an image based on said generated predicted image when operation contents of an input operation match those of said predicted information,
wherein the predicted information is an operation information obtained by changing a selected one-dimensional parameter, and further wherein the predicted image generating section generates the predicted image based on the operation information obtained by changing the selected one-dimensional parameter, and wherein the one-dimensional parameter of the operation information which is obtained by changing the one-dimensional parameter is a look-up table parameter, wherein the one-dimensional parameter of the operation information which is obtained by changing the one-dimensional parameter is one of the parameters for defining an opacity function.

12. An image processing apparatus comprising:
a predicted information storage section for storing a predicted information indicating operation contents which are predicted for an image of a target operation;
a predicted image generating section for generating a predicted image based on the predicted information so as to be corresponding to the image of the target operation;
an image display control section for displaying an image based on said generated predicted image when operation contents of an input operation match those of said predicted information;
a history information storage section for storing a history information which indicates the operation contents performed in the past,
wherein the predicted information is generated based on the history information,
wherein the predicted information is a preceding operation content,
wherein the predicted image generating section generates one or more predicted image based on the preceding operation content, and wherein the predicted image generating section generates the volume rendering image that is obtained by the pan operation which is determined by changing a two-dimensional parameter, when the preceding operation content is a pan operation such that a volume rendering image of the target operation is moved two-dimensionally parallel to a projection plane without changing the projection angle of the volume rendering image.

13. An image processing apparatus according to claim 12, wherein the predicted image generating section generates the predicted image by distributing a calculation load, requiring for generating the predicted image, to a plurality of image processing apparatuses connected via a network.

* * * * *